United States Patent [19]

Webb

[11] Patent Number: 4,992,644

[45] Date of Patent: Feb. 12, 1991

[54] DEVICE FOR STERILIZATION, STORAGE AND DISPENSING OF LIQUIDS

[76] Inventor: Garth T. Webb, 31521 Brookside Ave., Clearbrook, Canada, V2S 6A9

[21] Appl. No.: 403,307

[22] Filed: Sep. 5, 1989

Related U.S. Application Data

[63] Continuation-in-part of Ser. No. 181,238, Apr. 13, 1988, abandoned.

[30] Foreign Application Priority Data

Apr. 12, 1989 [CA] Canada .................................. 596540

[51] Int. Cl.$^5$ .......................... H05B 1/02; F24H 1/20
[52] U.S. Cl. .................................. 392/441; 219/492; 219/440; 422/146.1; 422/146.5; 422/95; 422/307; 422/905
[58] Field of Search ............................. 219/310–315, 219/323, 327, 440, 492, 497; 222/146.1, 146.2, 146.5, 153, 95, 96; 422/307, 905

[56] References Cited

U.S. PATENT DOCUMENTS

| | | | |
|---|---|---|---|
| 2,700,094 | 1/1955 | Hosack ................................. | 219/19 |
| 2,806,123 | 9/1957 | Steinbock, Jr. ..................... | 219/309 |
| 3,614,386 | 10/1971 | Heppleuhite ........................ | 219/312 |
| 3,801,278 | 4/1974 | Wagner .............................. | 219/439 |
| 3,865,277 | 2/1975 | Rimini .......................... | 222/146 HE |
| 3,973,760 | 8/1976 | Browning et al. .................. | 219/328 |
| 4,263,498 | 4/1981 | Meyers ............................... | 219/312 |
| 4,481,410 | 11/1984 | Bortnick ............................. | 219/521 |
| 4,844,927 | 7/1989 | Morriss, II et al. ................. | 219/312 |

FOREIGN PATENT DOCUMENTS

55-65857 5/1980 Japan .

*Primary Examiner*—M. H. Paschall
*Attorney, Agent, or Firm*—Kelly, Bauersfeld & Lowry

[57] ABSTRACT

A safe, portable apparatus for sterilization of saline or other liquids is provided. There is provided a device for sterilizing and storing liquids comprising a housing, a hollow cyliner formed in the housing having an open first end and a closed second end, a piston sealingly mounted for sliding within the cylinder, the piston and the cylinder thereby forming a closed chamber for receiving the liquid, the chamber provided with a sealable opening for introducing the liquid to the chamber, means for biasing the piston into the cylinder thereby applying pressure to the liquid, means within the housing for heating the liquid, and fluid discharge means for discharging the liquid when sterilized.

18 Claims, 14 Drawing Sheets

DEVICE FOR STERILIZATION, STORAGE AND DISPENSING OF LIQUIDS

This is a continuation-in-part of application Ser. No. 181,238 filed Apr. 13, 1988, now abandoned, entitled Device for Sterilizing Liquids.

BACKGROUND OF THE INVENTION

The invention relates to devices for sterilizing liquids, and more particularly to devices for sterilizing and storing saline for ophthalmic purposes, particularly for contact lens applications.

Sterile saline is required by contact lens wearers for use as a rinse solution prior to inserting the lens in the eye, and also for soaking the lens during the sterilization process. The sterility of the solution is important to avoid eye infection. There are several methods of sterilizing and storing saline presently in use. In some cases an autoclave, a device which sterilizes using steam under pressure is used or a heat kit applying electric heat directly to the saline container may be used. One method of storing sterile saline is accomplished by sterilizing small sealed single unit dose plastic packages. Larger plastic bags of solution for intravenous applications may be treated in a similar fashion, but once these containers have been opened, the entire contents must be used immediately and the rest discarded as the saline loses its sterile character.

Heat kits are known which sterilize saline contained in plastic squeeze containers. See for example U.S. Pat. No. 3,801,278 issued Apr. 2, 1974 to Sybron Corporation and U.S. Pat. No. 4,481,410 issued Nov. 6, 1984 to Bortnick. In these devices, the plastic bottles of solution are simply heated within an enclosure to 85-90 degrees Celsius and maintained at that temperature for about 10 minutes. Once the plastic containers have been opened it is necessary to resterilize them before using again. It is also known to use ultrasonic waves to sterilize contact lenses and saline. See U.S. Pat. No. 3,973,760 issued Aug. 10, 1976. The ultrasonic waves heat the solution more gently but over a longer period of time than the heat kits noted above. None of the foregoing apparatus, however, is capable of storing the sterilized saline so that it maintains its sterile character after an initial use.

Sterilized saline for contact lens use has more recently been made available in aerosol cans. This provides an effective method of storage as the internal contents are kept free of contamination by the positive pressure within the can. The expense and environmental problems associated with aerosol spray cans make this a less attractive alternative.

There is therefore a need for an inexpensive supply of sterile saline which can be stored and reused without losing its sterile character. The present invention provides a compact and portable device for providing such a renewable supply of sterile saline.

SUMMARY OF THE INVENTION

The invention provides a safe, portable apparatus for sterilization of saline or other liquids. There is provided a device for sterilizing and storing liquids comprising a housing, a hollow cylinder formed in the housing having an open first end and a closed second end, a piston sealingly mounted for sliding within the cylinder, the piston and the cylinder thereby forming a closed chamber for receiving the liquid, the chamber provided with a sealable opening for introducing the liquid to the chamber, means for biassing the piston into the cylinder thereby applying pressure to the liquid, means within the housing for heating the liquid, and fluid discharge means for discharging the liquid when sterilized.

BRIEF DESCRIPTION OF THE DRAWINGS

In drawings which illustrate a preferred embodiment of the invention.

DETAILED DESCRIPTION OF A PREFERRED EMBODIMENT

Figures 1, 1A:
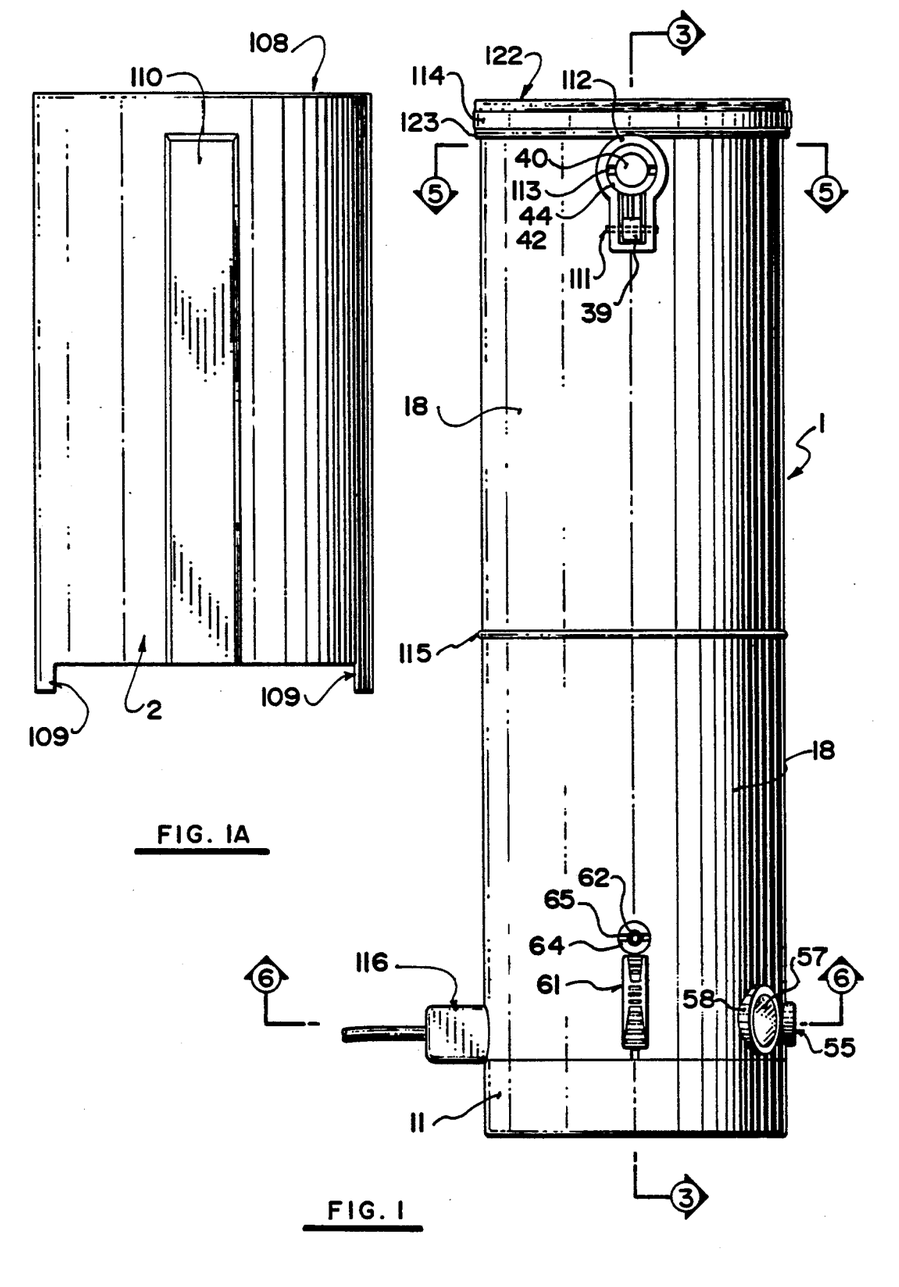
FIG. 1 is a front view of the invention, with the cover removed.
FIG. 1A is a front view of the cover of the invention.

Referring to FIG. 1, the device of the invention is designated generally as 1, with a removable cover 2, shown in FIG. 1A. The housing 18 and cover 2 of the device are manufactured of a rigid heat resistant moulded plastic.

Figures 2, 2A:
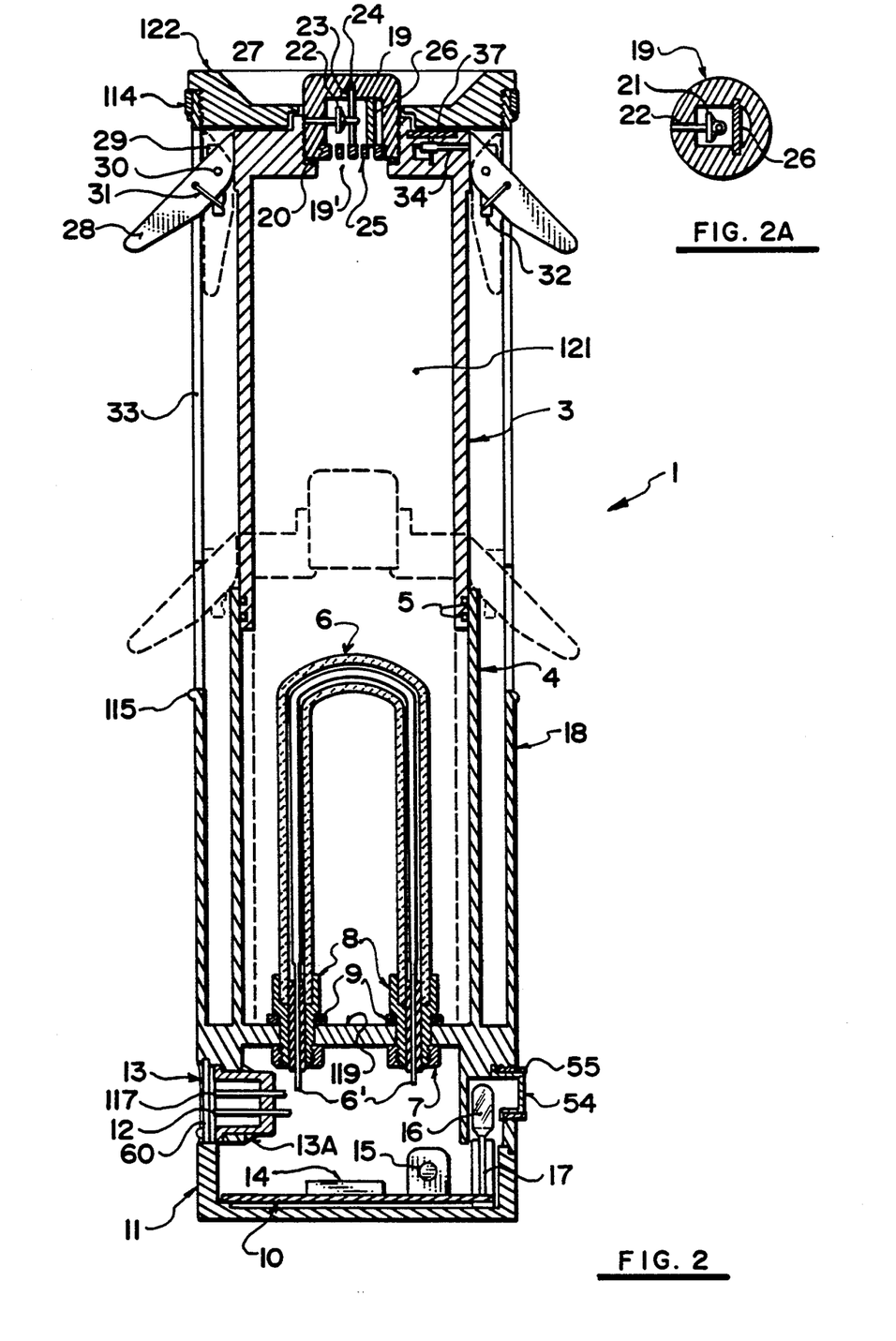
FIG. 2 is a vertical cross section taken along lines 2—2 of FIG. 1B.
FIG. 2A is a horizontal cross section of cap 19 in FIG. 2.

FIG. 2 shows hollow cylindrical piston 3 that slides within vertical cylinder 4. Both are also constructed of heat resistant moulded plastic. The piston is sealed against the inside surface of the cylinder by rubber 'O' rings 5. FIG. 2 shows the piston in its two extreme positions, with the lower position in broken outline. A heating element 6 is mounted on the base 119 of cylinder 4 and is secured by two nuts 7 which are threaded onto two threaded metal supports 8 attached to the legs of heating element 6. A set of rubber washers 9 are mounted between the metal support and base 119 to provide a watertight seal. The two electrical terminals 4a protrude into the sealed cavity 129 as shown. This sealed cavity houses all of the electrical components.

Figure 3:
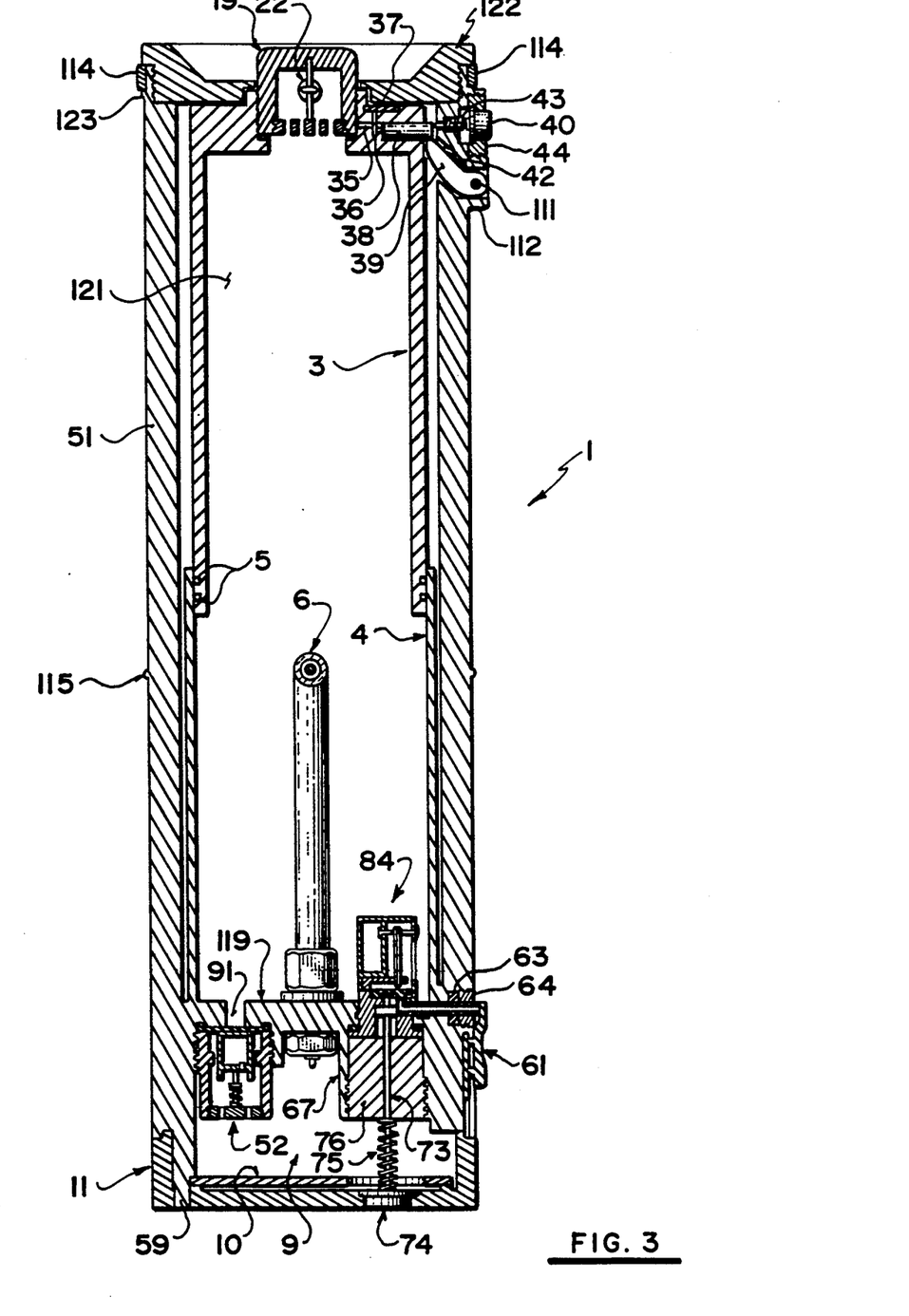
FIG. 3 is a vertical cross section taken along lines 3—3 of FIG. 1.
Figure 4:
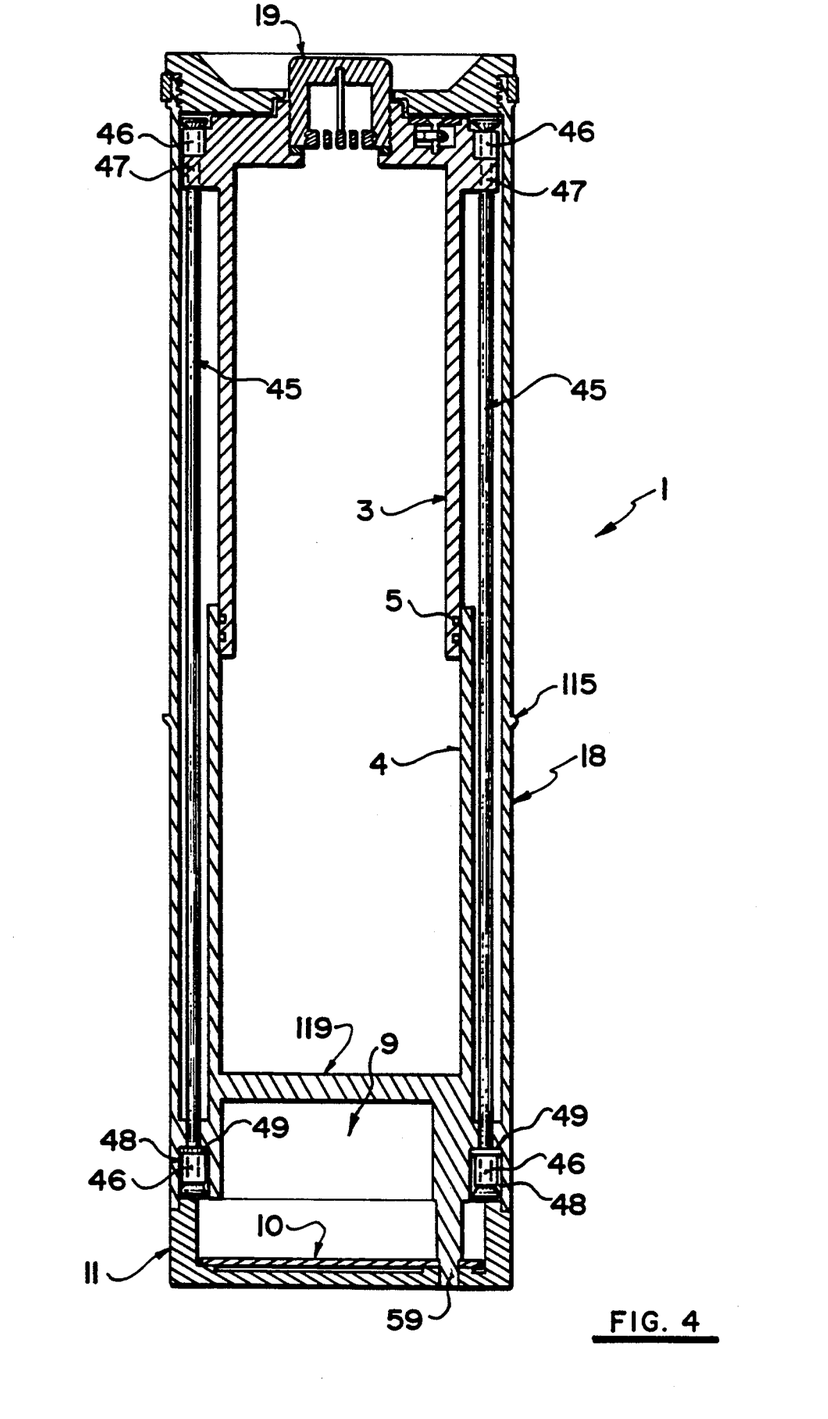
FIG. 4 is a vertical cross section taken along lines 4—4 of FIG. 5.

A printed circuit board 10 is mounted on end cap 11. All of the electrical components, including terminals 4a, are connected in a circuit with this circuit board except for the ground wire 12 which is connected to a terminal 101 on the pressure sensitive switch shown in FIG. 11. A three pronged electrical outlet 13 is snapped into an orifice in the outer casing 18 and held there by small flanges 13A as shown in FIG. 2. An electronic clock circuit 14, a fuse 15 and a light bulb 16 are shown mounted on printed circuit board 10. The light bulb is held in position by support 17. FIGS. 2 through 4 show that the outer casing 18 may be moulded as a unitary element of heat resistant plastic with the inner cylinder 4.

A hollow, cylindrical cap 19 screws into threaded orifice 19' in the top of hollow piston 1 and seals the orifice watertight by forcing washer 20 against shoulder 20'. A horizontal cross section of the cap is shown in FIG. 2a. The cap houses a rubber plug 21 which is mounted on a metal peg 22 which extends outwardly through an aperture in the cap. The metal peg is flattened on one end to make a watertight seal with the rubber plug and extends further to form a small hoop through which a resilient filament 23 extends. The resilient filament is fixed in cap 19 at one end 24 and at the other end is fixed to fenestrated end piece 25 which screws into the open end of the cap. The crossplate 26 is positioned to keep the metal peg from sliding too far into the cap.

When the volume within the hollow piston 3 becomes pressurised, the metal peg 22 is pushed outwardly through a slots 27 in the rim of the orifice 19' and prevents the cap from being unscrewed. When the unit is not pressurized the peg returns to the rest position shown in FIG. 2.

FIG. 2 also shows a pair of retractable arms 28 which are shown in both the retracted extended positions, the latter position being shown in bold lines. The retractable arms are pivotally mounted on a pair of plastic extensions 29 of the piston 3 by two metal pins 30. A small rubber band 31 is threaded through a hole in each retractable arm as shown. The rubber band is then looped under two small finger-like projections 32 to bias the arm inwardly. When the piston 3 is pulled down the cylinder 4 the retractable arms eventually contact the top of the cylinder and are extended outwardly through slots 33 in the outer casing 18.

Figure 5:
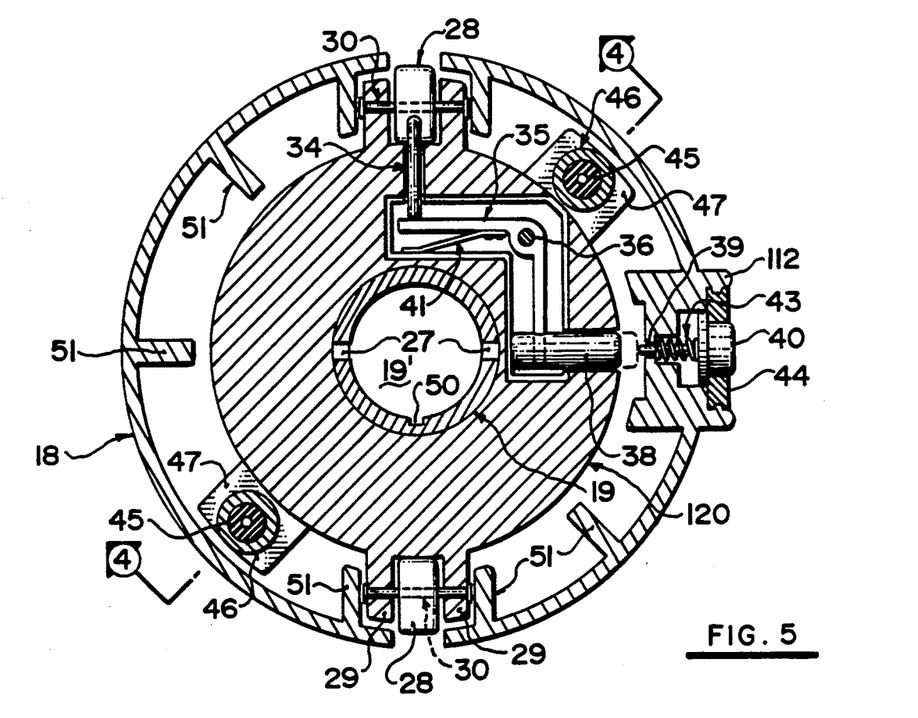
FIG. 5 is a vertical cross section taken along lines 5—5 of FIG. 1.

Two pieces of rubber band or tubing 45 provide pressure to the piston to draw it into the cylinder and pressurize the contents. Means are therefore provided to lock the piston in the raised position for filling. When retractable arms 28 are extended, a small push-rod 34 is depressed inwardly by the retractable arms and presses down on the 'V'-shaped first-class lever 35 which has its fulcrum secured by a metal screw 36 that also holds cover plate 37 in position. This is best seen in FIGS. 3 and 5. FIG. 5 shows the first-class lever fitted through a notch in the locking peg 38. When the push-rod pushes down on the 'V'-shaped first-class lever, the locking peg is pushed beyond the flattened surface 120 of the piston and catches onto the locking arm 39. The locking arm is normally biassed towards the piston by a spring 42 and is pivotally secured to the housing protrusion 112 by rivet 111. The locking arm thus holds the piston in the upper position by bearing against the underside of peg 38. The arms 28 are then free to retract inwardly against the side of the piston while the unit is being re-filled.

Once the unit has been re-filled and the cap replaced, the user presses release button 40. The release button pushes the locking peg back behind flattened surface 120 of the piston so that the rubber tubing 45 is free to pull the piston downwardly, thereby pressurizing the internal compartment 121. A spring 41, shown in FIG. 5 biases the first-class lever so that the locking peg is forced to stay below the flattened surface 120 until the retractable arms push the peg out again. When release button 40 is released, a coil spring 43 pushes the release button outwardly until it abuts against a threaded metal ring 44. The metal ring has two slots 113 which allow it to be tightened into the housing protrusion 112 which protrudes out from the outer casing 18.

FIG. 4 shows the rubber tubing 45 which supplies the mechanical pressure on the piston in the downward direction. The rubber tubing is approximately 5 cm. long when at rest and is stretched the length of the unit as shown. The ends are grasped by cylindrical metal clasps 46 that are crimped around the tubing so as to grip securely even when the rubber has been stretched to its maximum. The rubber tubing extends through holes 47 and 48 with the clasps 46 being wider than and bearing against the surface of projections 47 and casing 18. This structure prevents the tubing from slipping out of its position on the piston. Similarly, at the base of the unit, the metal clasp 46 is held down by a rigid rubber washer 49 through which the tubing passes. This washer 49 also acts as a watertight seal.

In FIG. 5 a small channel 50 is shown which runs down the inner surface of the orifice 19' so that pressure does not build up inside the unit when the cap is being screwed into position. Also shown in FIG. 5 are a number of vertically extending ribs 51 which provide rigidity to the walls of the outer casing 18.

Figure 6:
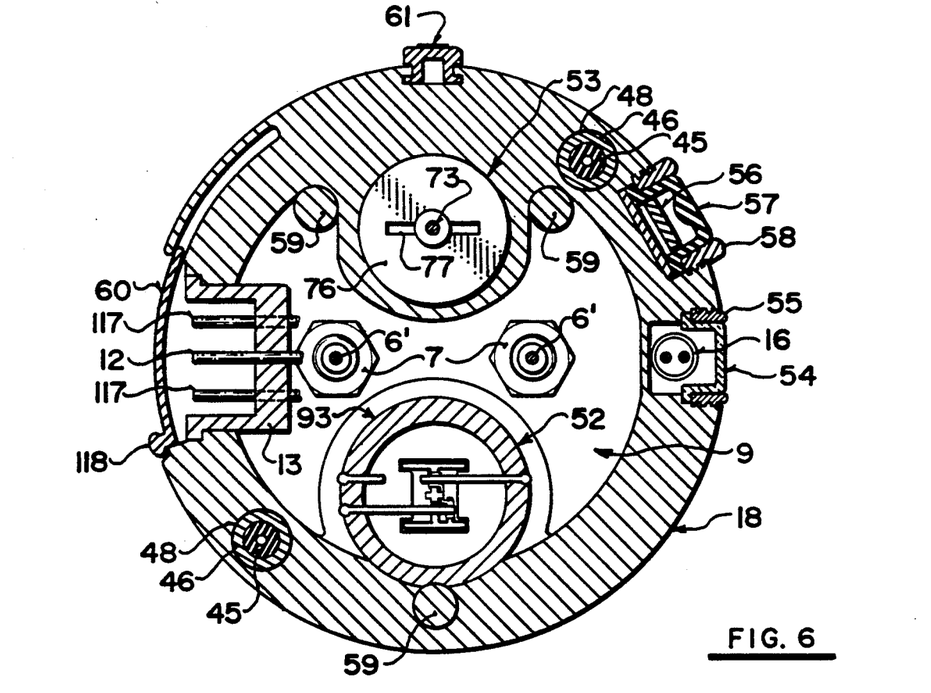
FIG. 6 is a vertical cross section taken along lines 6—6 of FIG. 1.

FIG. 6 represents a horizontal cross-section of the base of the sealed compartment 9. The positions of the fluid delivery mechanism 53 and the pressure sensitive electrical switch 52 are shown. The translucent light cover 54 is held in position by threaded nut 55. The master on-off switch 56 and switch cover 57 are similarly held in position by threaded nut 58. Three circular plastic projections 59 are shown. These projections of the housing are fitted through openings in the end cap 11 and then melted with a soldering iron to secure the end cap. This prevents tampering with the electrical components.

Figure 1B:
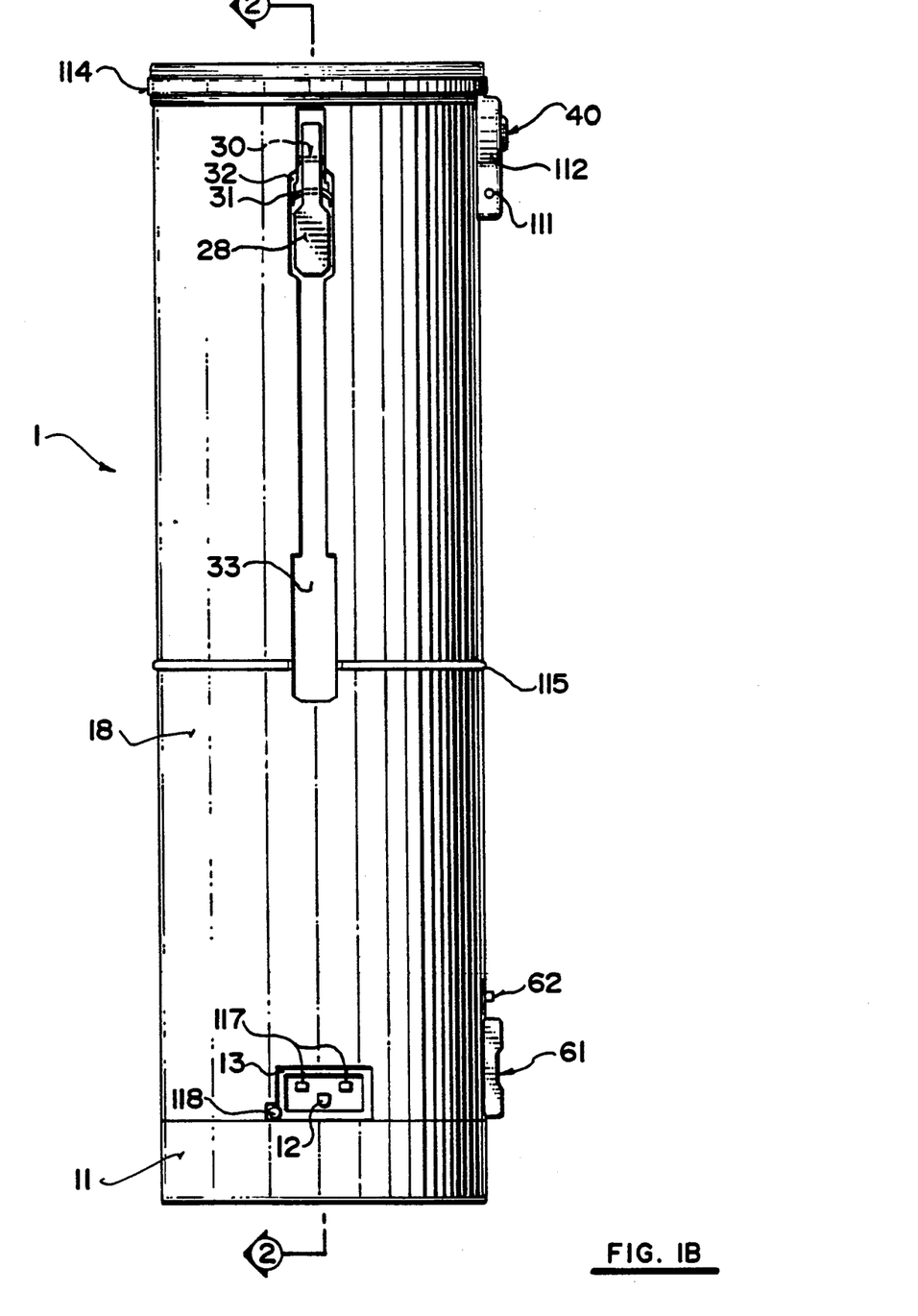
FIG. 1B is a left side view of the invention with the cover removed.

A sliding cover plate 60 is provided to protect the electrical terminals when the electrical cord 116 is not plugged in. Knob 118 attached to the sliding cover plate 60 as shown in FIG. 1b facilitates the sliding of the plate. A sliding cover 61 also serves to cover the end of the fluid discharge tube 62. A watertight seal is produced around the circumference of the discharge tube 62 by the rubber washer 63 shown in FIG. 3. Threaded ring 64 holds the washer and tube firmly in place. Slots 65 on each side of ring 64 facilitate its tightening.

Figure 7:
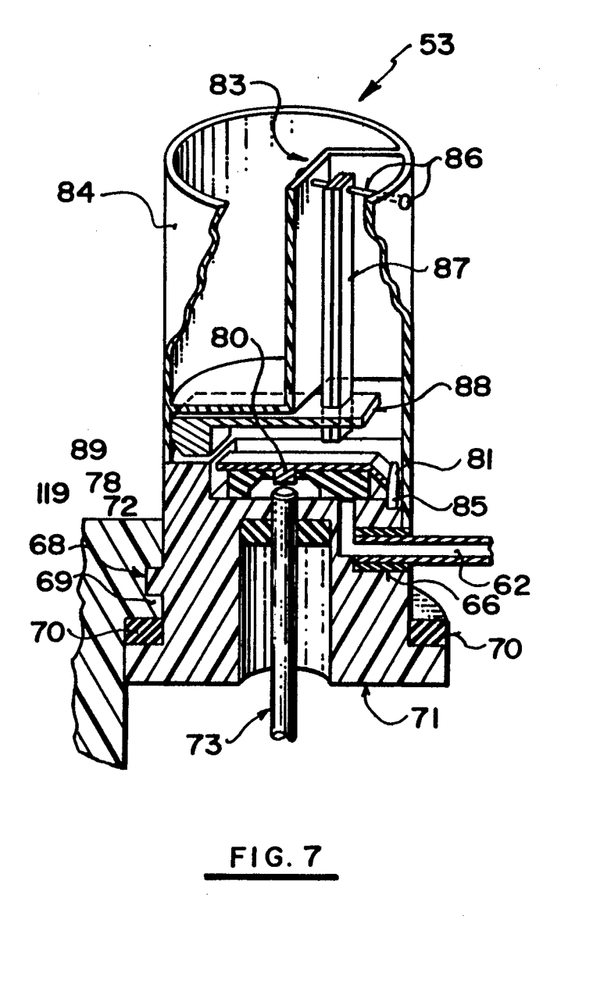
FIG. 7 and FIG. 8 are enlarged isometric views of the fluid discharge device of the invention, partially in section.
Figure 8:
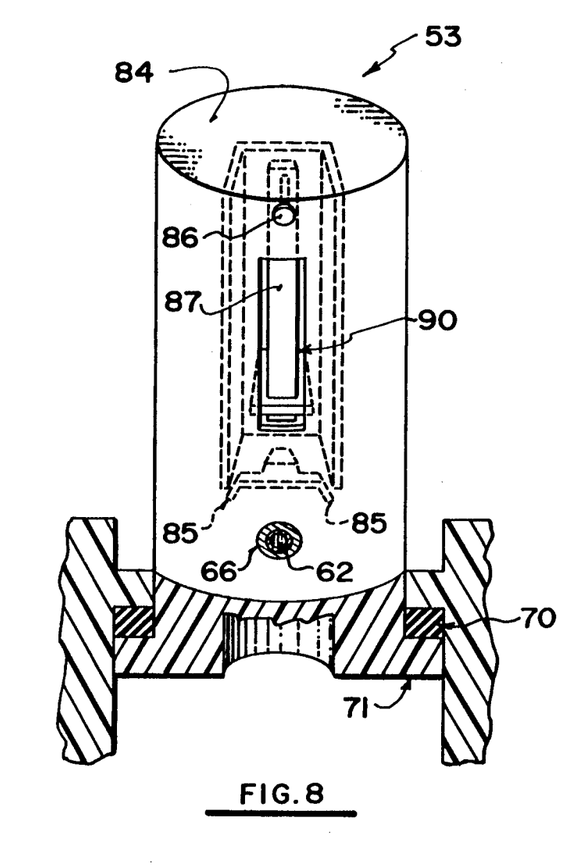
Figure 8A:
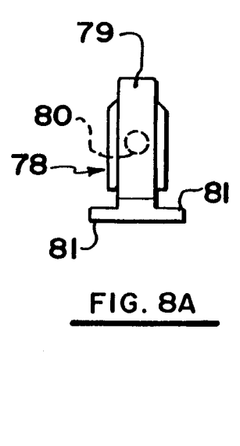
FIG. 8a is a top view of the valve shown in FIGS. 7 and 8.

Referring to FIGS. 7 and 8, a plastic sleeve 66 provides a watertight seal between the metal discharge tube and the body of valve housing 67. A small projection 68 fits into a slot 69 of base 119. This aligns the body of the discharge valve with the hole in the side of the unit through which the discharge tube 62 is inserted. A washer 70 is fitted around the feet of the valve housing 71 to provide a watertight seal. A small rubber washer 72 provides a watertight seal around the shaft 73 of the discharge button 74. The discharge button is biassed outwardly by coil spring 75 which is seated on the threaded plug 76. There is a slot 77 on the top of the threaded plug by which the plug is tightened against the rubber washer 70 in the valve housing 67. A cross-section of the rubber valve 78 is shown in FIG. 7 and a top view is illustrated in FIG. 8A. The rubber valve 78 is held on the valve support 79 by a projection or pedestal 80 as shown on FIG. 7. The valve support is free to pivot around the axes 81 which are free to rotate in channel 82 at the bottom of the plastic insert 83.

A safety mechanism is provided to prevent the discharge of hot liquid. The plastic insert is pressed against the body of the valve housing 84 by two tabs 85 and the rivet 86 shown in FIGS. 7 and 8. The rivet holds the insert in position but it also secures a bi-metal strip 87, holding it against the body of the valve housing. The other end of the bi-metal strip is directed through a slot in the neck of sliding bar 88 and then is folded over to lock it into position. The bi-metal strip pulls the head 89 of bar 88 over the top of the valve support when the temperature of the liquid is greater than 50 degrees Celsius so that the valve cannot be opened. This mechanism operates without any electrical current so the user cannot scald himself even if the electrical cord 116 has been disconnected. The head 89 of the sliding bar cannot be moved beyond the pedestal as the end of the bar would abut against the wall of the plastic insert as shown in FIG. 8. The slot 90 in the plastic insert guides the fluid into the space between the body of the valve housing 84 and the plastic insert so that the bimetal strip can bend in response to changes in temperature of the liquid.

The slot 90 has also been positioned above the axes 81 of the valve support so that the valve is forced to close by the movement of the pressurized fluid. The valve remains closed unless the discharge button 74 is pressed or if the internal compartment 121 has been depressurized. When the unit is ready to be refilled the piston is pulled upwardly by the retractable arms. This creates a vaccum within the inner chamber 121 which opens the rubber valve 78. The vaccum forces air into the inner chamber and cleans the discharge tube 62. The discharge tube is made of a heat-conductive metal such as silver so that the tube is sterilized by the relatively high temperatures achieved within the unit when it is turned on.

Figure 9:
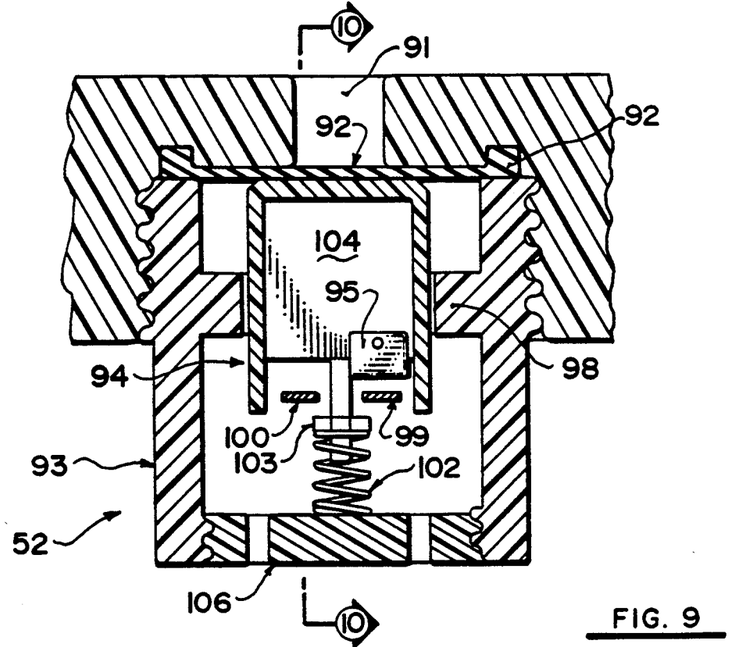
FIG. 9 is a vertical cross section taken along lines 9—9 of FIG. 11.
Figure 10:
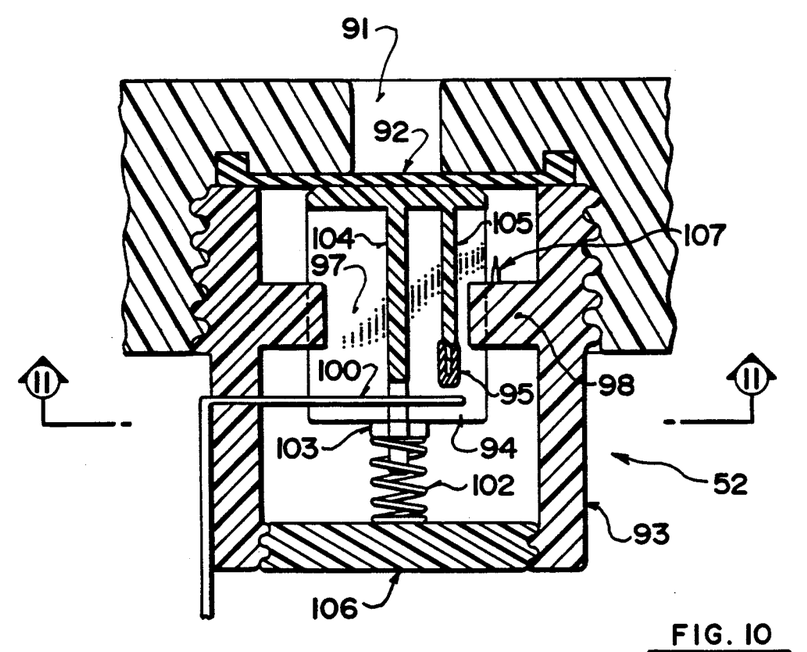
FIG. 10 is a vertical cross section taken along lines 10—10 of FIG. 11.
Figure 11:
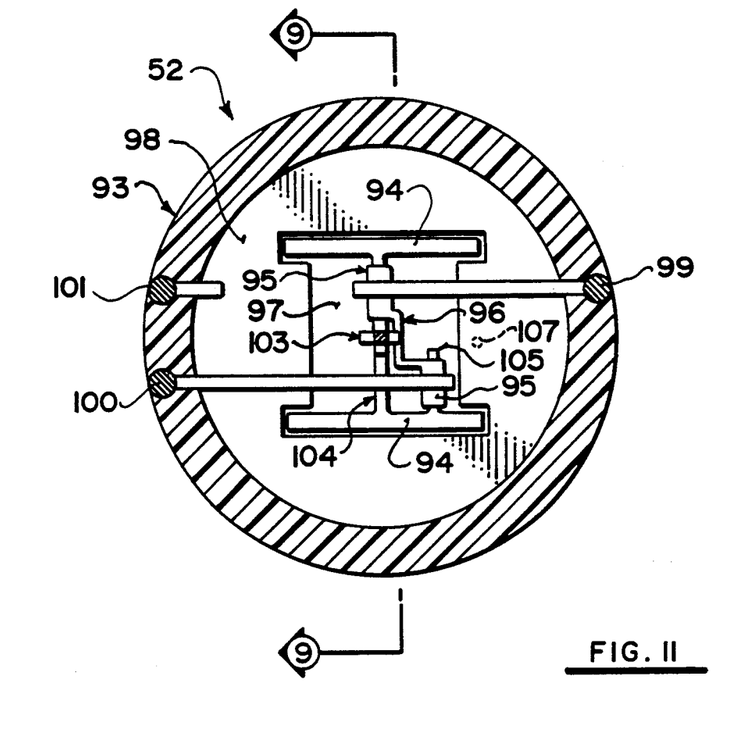
FIG. 11 is a horizontal cross section taken along lines 11—11 of FIG. 10.
Figure 12:
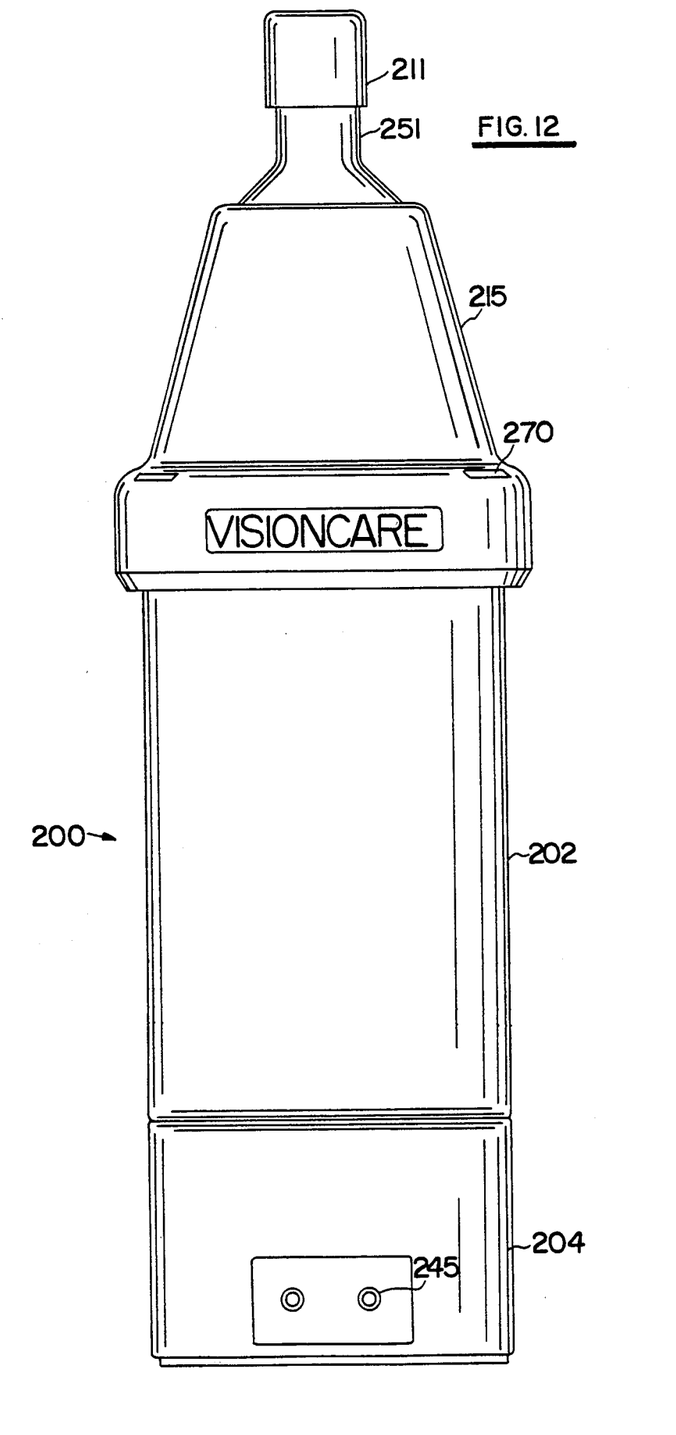
Figure 13:
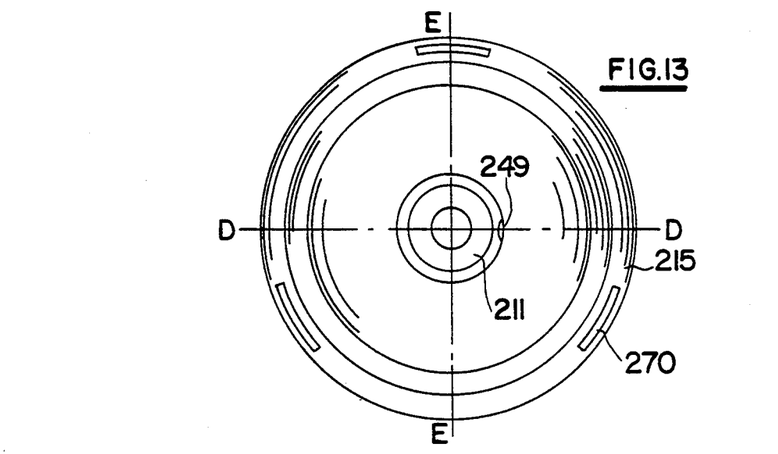

A pressure sensitive electrical switch, shown in FIGS. 3, 9, 10 and 11, acts both to ensure that the heater will not be activated until the unit has been filled and pressurized, and as a safety switch and pressure release valve to cut off electrical power to the heating element when the pressure in inner chamber 121 exceeds a certain point and to release the liquid when the pressure is dangerous. FIGS. 9 and 10 depict vertical cross-sections and FIG. 11 shows a horizontal cross-section of the mechanism. A passageway 91 in the base of the cylinder 4 is sealed by a rubber diaphragm 92 which is held in position by a threaded switch housing 93. The two electrical contacts 95 and interconnecting metal strip 96 are mounted onto the plastic slide 94. The plastic slide is free to slide through the 'H'-shaped aperture 97 which penetrates the dividing wall 98 of the switch housing 93. The plastic slide pushes the two electrical contacts onto the electrical terminals 99 and 100 when the rubber diaphragm expands in response to the unit being pressurised. This closes the switch, which in turn provides current to the heating element. The positive terminal 99 is located on one side of the switch housing and the negative terminal 100 on the other side of the housing. A ground 101 connected to ground 12 is provided for safety purposes should the switch fill with water and short circuit.

The pressure sensitive switch is opened when the unit is depressurized. In this case the rubber diaphragm reverts back to its rest position as shown. The plastic slide is pressed against the rubber diaphragm by coil spring 102 which is bears against cross-piece 103 at one end and against the fenestrated cover 106 at the other. Cross-piece 103 is a finger-like projection extending from a supporting rod connected to central cross-bar 104. The central cross-bar 104 carries the electrical contact 95 that contacts positive terminal 99. The other electrical contact 95 is carried by rib 105.

The pressure sensitive switch can also be opened if the rubber diaphragm continues to expand as a result of elevated pressures within the unit. The plastic slide 94 is pushed toward the fenestrated cover 106 until the cross-bar engages the negative terminal 100. As the negative terminal is pushed further downwardly by the cross-bar it disengages from the electrical contact 95. This allows the liquid to cool so that pressure is reduced in chamber 121. The rubber diaphragm recedes and once again the switch is closed. The switch opens and closes several times before the clock 14 turns the unit off. A complete cycle would last approximately twenty minutes.

A small pointed projection 107 is shown in FIG. 10. This pin bursts the rubber diaphragm if the pressure sensitive switch should ever fail. This would allow water to enter into the switch and cause a short circuit and causing the fuse to break the circuit. The thickness of the rubber diaphragm is selected so that pin 107 would prick the diaphragm at approximately twenty pounds per square inch of internal pressure.

The resistance of the coil spring 102 is selected so that the switch is opened when the internal pressure is between zero and two pounds per square inch above atmospheric pressure. The switch is closed when the internal pressure is between two and fifteen pounds per square inch above atmospheric and opened again when the pressure exceeds fifteen pounds per square inch above atmospheric.

The protective cover 108 is designed to snap over ridge 115 when the unit is being transported. The two tabs 109 are tapered so that they do not lock onto the retractable arms when the arms are pushed outwardly. The channel 110 is designed to fit over top of the release button and its surrounding housing. The three-pronged electrical cord 116 fits into receptacle 13 and connects with the ground wire 12 and the two other terminals 117 shown in FIG. 1b.

A brass ring 114 supplies the rigidity that the top plate 122 requires to resist the potential forces that may be exerted upon it if the internal pressure is raised to a sufficient degree. The brass ring is held in position by the top plate 122 and the top lip 123 of the outer casing.

In operation, the user fills the unit with non-sterile saline by grasping the two arms 28 and raising the arms and attached cylinder until locking peg 38 snaps over locking arm 39 to hold the piston in the upper position. A predetermined amount of water and salt tablets is then poured into chamber 121 through orifice 19'. Once filled, cap 19 is replaced and release button 40 pressed, allowing the piston 3 to be drawn down by rubber bands 45, thus pressurizing the contents of chamber 121. The increased pressure causes valve 53 to be closed and switch 52 to be closed. The master on-off switch 56 may now be pressed to complete the circuit, providing current to heating element 6, starting clock 14, and illuminating indicator light 16. Switch 53 keeps the pressure, and hence the temperature in the chamber 121 within a predetermined elevated range appropriate for the sterilization of saline during this period. After the programmed heating period has elapsed, the clock shuts off power to the heating element, light 16 is turned off, and the contents of chamber 121 begin to cool. Once the liquid is sufficiently cool, the user can dispense the liquid by depressing button 74.

As the contents of the unit are used up, the piston lowers in cylinder 4, but the contents remain under pressure. As outside air cannot contact the pressurized contents, the stored saline remains substantially sterile. As the piston reaches the lower extremity of its travel, arms 28 begin to extend and the user sees that it is time to refill the device. Once the piston has bottomed out against the base of the unit, and the pressure released through the discharge valve, the filling cap can be removed and the cycle repeated.

Thus the invention provides a sealed, pressurised cannister for sterilizing and storing saline that incorporates a pressure sensitive electrical switch which controls the internal temperature for a predetermined period of time. The electrical circuit is not closed until the cannister is pressurized and the pressurization cannot occur if the filling cap is not tightly secured. Once pressurized, the cap is locked into position and it cannot be removed until the cannister is depressurized. The cannister cannot be depressurized until the piston is pushed down to the bottom of the shaft. The saline cannot be dispensed until sufficiently cool. The discharge tube is sterilized each time the unit is refilled. These features make the device a safe, effective apparatus for sterilization of liquids, particularly saline.

As will be apparent to those skilled in the art, various modifications and adaptations of the structure described above may be made without departing from the spirit of the invention. For example, the invention need not to be limited to the autoclave principle. The autoclave has been selected as it provides the most effective and the least expensive form of sterilization. It is possible, for example, to mount an ultraviolet-emitting radiator within the container to sterilize the liquid. With the use of an appropriate timing device, the modified unit would otherwise work in the same way. Another possible variation, without altering the basic concept of the invention, would be to sterilize the liquid at temperatures below the boiling point of water with a heating element and then utilize a temperature-sensitive switch instead of a pressure-sensitive switch as a thermostat. Another possible variation of the structure would be to mount the sterilizing energy source outside of the container. Consequently the scope of the invention is to be defined by reference to the appended claims.

A second preferred embodiment of the invention is shown in FIGS. 12 through 19. In this embodiment, pressure is applied to the liquid contents by a spring-driven piston, rather than the rubber tubing discribed in the previous embodiment.

Figure 14:
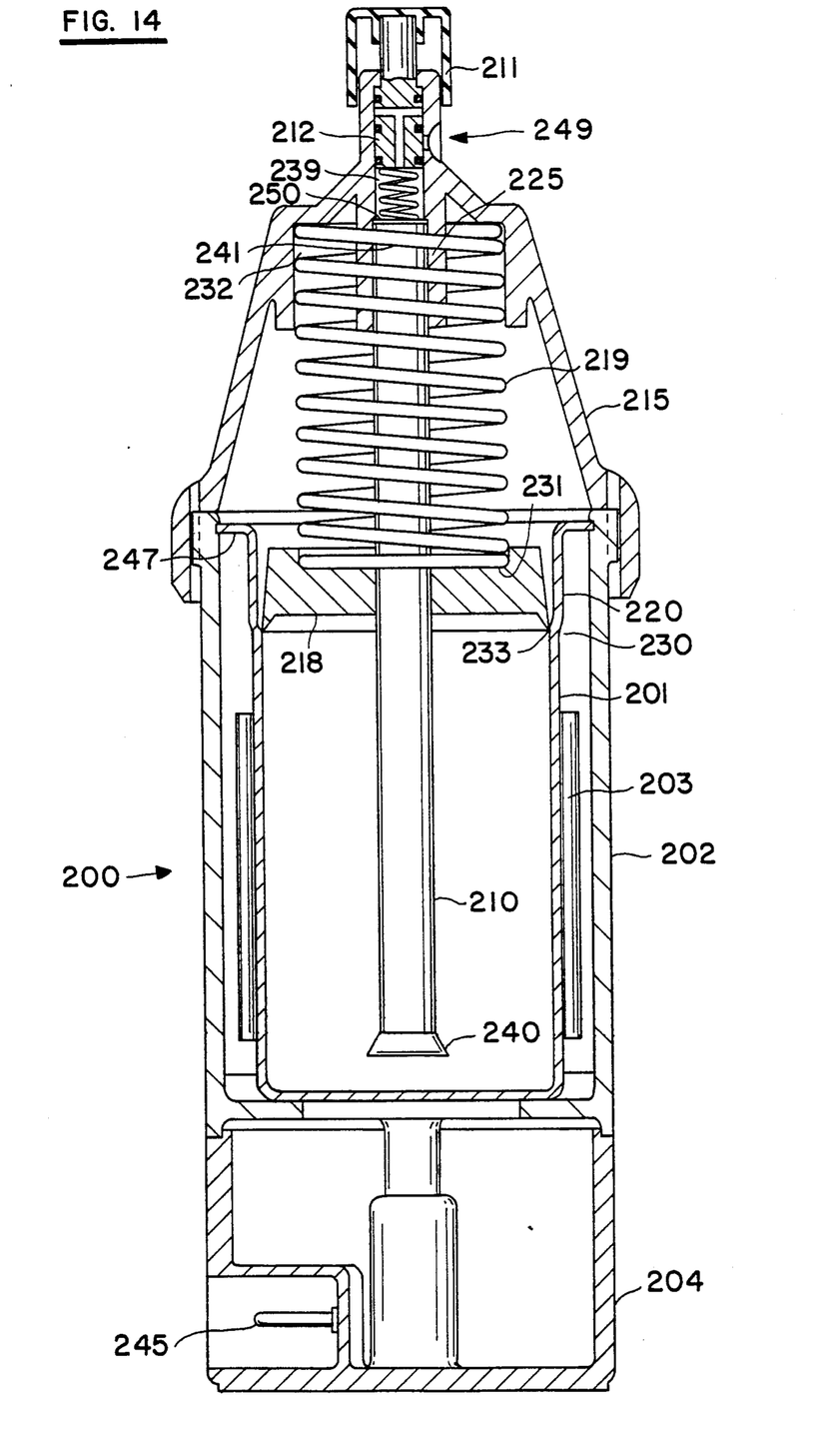
Figure 15:
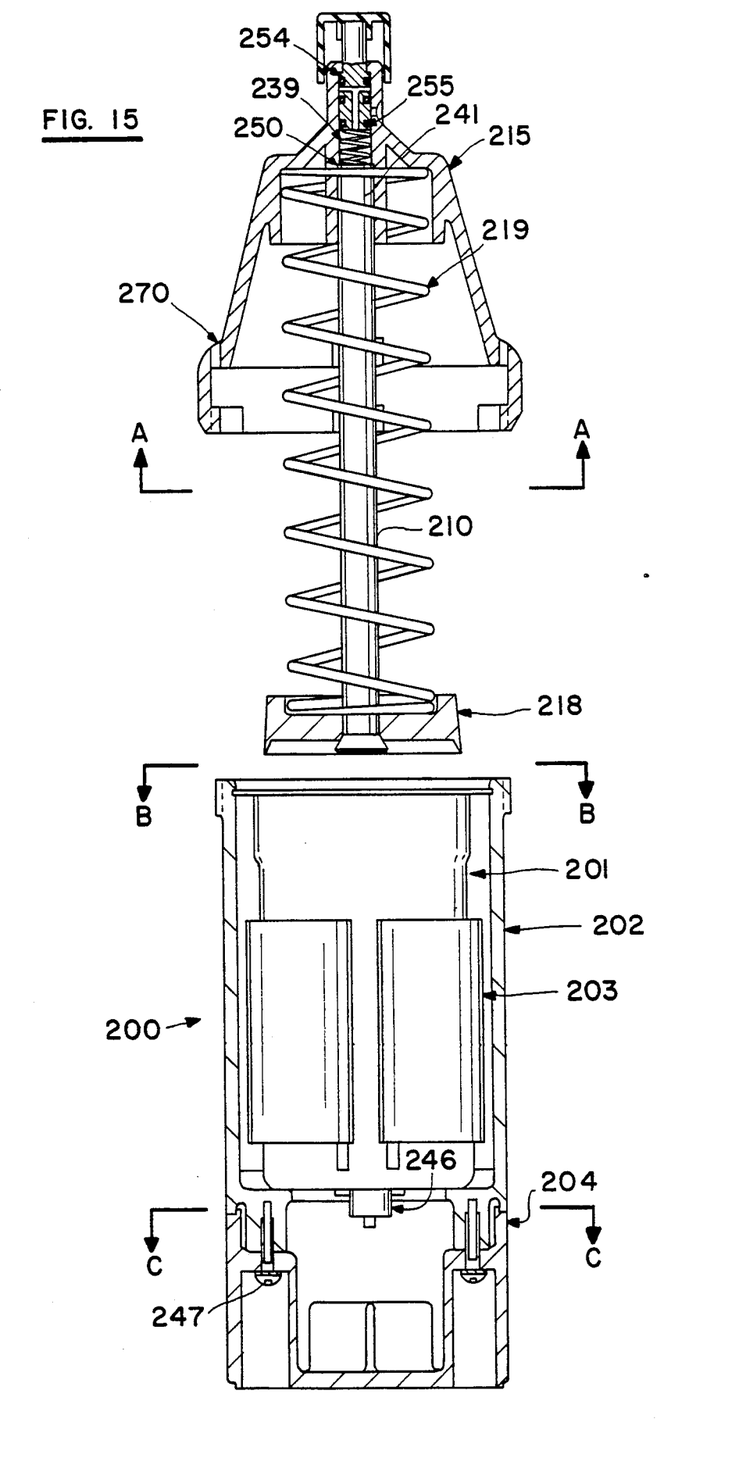
Figure 16:
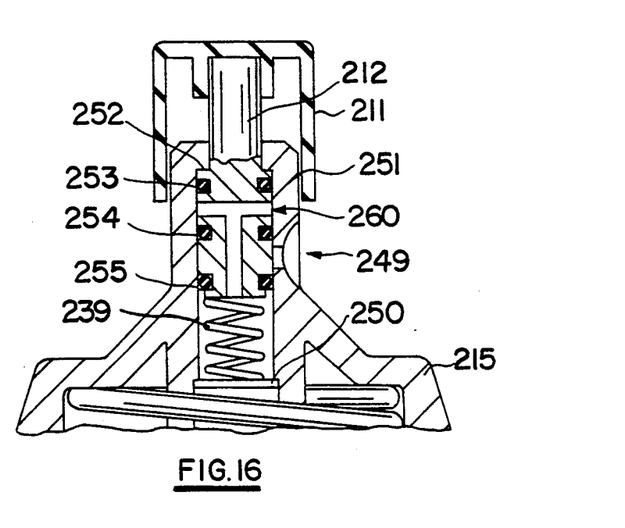
Figure 17:
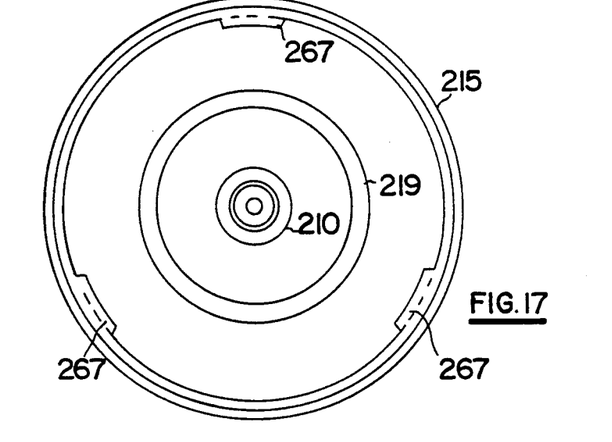
Figure 18:
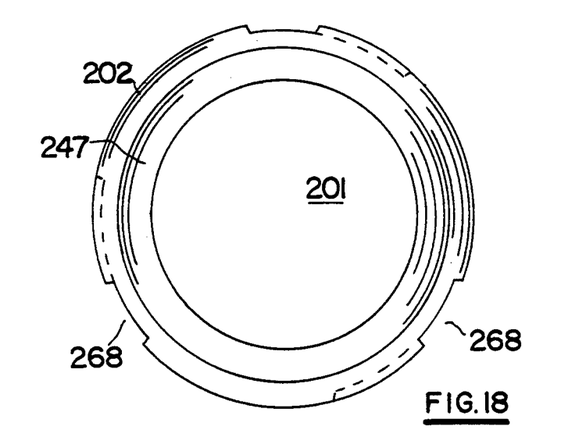
Figure 19:
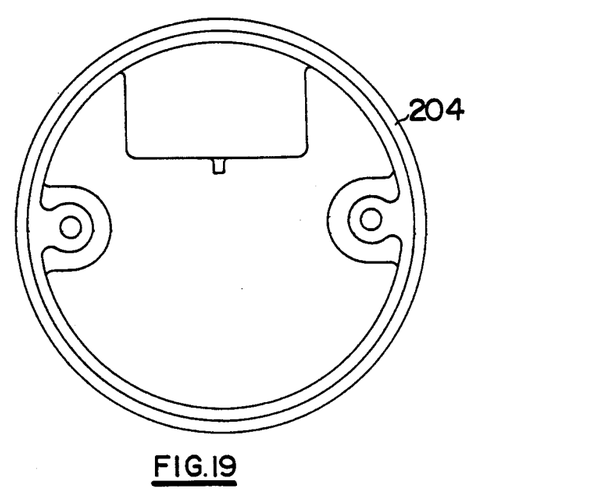

Referring in particular to FIGS. 14 and 15, the device for sterilizing liquids is designated generally as 200. It has a cap 215, a housing 202 and a base 204, all moulded from a tough heat-resistant plastic such as a polycarbonate. Mounted within the housing 202 is a hollow metal canister 201 of stainless steel or aluminum which opens upwardly to form a mouth which receives the liquid to be sterilized. The upper mouth area 220 of canister 201 is of slightly greater diameter than the lower cylindrical portion of the canister and the line of intersection of the two sections forms a shoulder 230. The upper edge of canister 201 extends outwardly to form lip 247 joining the inner wall of housing 202 and sealing the interior of the housing from above.

A hollow plastic tube 210 formed of a heat resistant plastic such as LEXAM TM is glued into cylindrical skirt 225 of cap 215. Both ends 240 and 241 of tube 210 are open. Sealed piston 218, which is formed of neoprene or similar flexible waterproof substance, slides sealingly on the tube 210 within canister 201. Piston 218 is driven by spring 219, one end of which seats in a depression 231 in the upper surface of the piston, and the other end of which seats in cavity 232 of cap 215. Piston 218 tapers outwardly and downwardly to form a lower lip 233 which slides sealingly along the inner wall of the lower section of canister 201 but which is smaller in diameter than the upper mouth portion 220. This structure allows excess pressure to be released. Flared end 240 on tube 210 prevents piston 218 from sliding completely off of the tube.

An electric heating element 203 is provided around the outer wall of canister 201. This is preferably a vulcanized silicone rubber heater of the type commercially available for medical heating applications, having a rubber encased heating coil. Electrical power for the heater is provided through electrical connection 245. A thermal detecting switch 246 deactivates the heater when canister 201 reaches a predetermined temperature. The electrical circuitry for supplying power to the heater 203 via switch 246 is known to those skilled in the art and is not shown. Base 204 is removably secured to housing 202 by screws 247, thereby allowing access to the electrical circuitry.

A second, smaller spring 239 is provided in cap 215, its lower end resting on flat washer 250, whose outer edges in turn rest on tube 210. Flat washer 250 has a central circular aperture to allow the passage of the liquid. Resting on the upper end of spring 239 is valve 212 which is connected to push button 211. Push button 211 forms an inverted cup which encircles the upwardly extending end 251 of cap 215. Shoulder 252 limits the upward travel of valve 212. A rubber O-ring 253 seals the valve below shoulder 252. O-rings are also provided at 254 and 255. Valve 212 has a central T-shaped aperture 260 having a vertical branch and a horizontal branch. End 251 of cap 215 has an outflow port 249 which aligns with the horizontal branch of aperture 260 thereby completing a passageway from the interior of canister 201 to the exterior of the device. It is desirable in such devices to limit the possibility of bacteria collecting at any point in the flow of the liquid. Here the two O-rings 254 and 255 are continually scouring the surfaces adjacent the outflow port which assists in achieving that end.

The lower edge of cap 215 is provided with three flanges 267 which engage corresponding slots 268 in the upper edge of the housing and slide under the outer edge 269 of the housing when rotated to lock the cap in place. Cap 215 is also provided with a number of slots 270 to allow the escape of steam.

In operation the cap 215 with attached piston is removed (by rotating and releasing the cap and simultaneously depressing the push button to release any vacuum) as shown in FIG. 15 and canister 201 is filled with the liquid to be sterilized. The cap is then replaced by sliding piston 218 into position in canister 201 and pressing down on the cap, thereby compressing spring 219, until flanges 261 engage in slots 262, at which point cap 215 is rotated and locked in position against vertical movement. Push button 211 is again depressed to release any air under pressure in tube 210. The heater 203 is then activated and regulated as desired. In the case of sterilizing contact lens solution, for example, the liquid is heated above 80 degrees Celsius and kept at that level for over 10 minutes. A timer may be included in the electrical circuitry for this purpose. Once the liquid is adequately sterilized it can be dispensed through port 249 by depressing push button 211. This opens the passageway between the interior of canister 201 and port 249 allowing the liquid under pressure to flow up tube 210 and out port 249.

While this embodiment has been described using an electrical heater, other means for sterilizing could be used, such as an ultra-violet radiator. Also it will be apparent that the piston arrangement could be replaced by a collapsible, possibly accordion-like, canister.

I claim:

1. A device for sterilizing and storing liquids comprising:
   (a) a housing;
   (b) a fluid discharge port;
   (c) a chamber formed in said housing for receiving and holding said liquid, and comprising an open end for introducing said liquid to said chamber and an inner wall;
   (d) a piston adapted to move within said chamber between a first and second position and having a pressure-applying face extending across said chamber for contacting and bearing against said liquid in said chamber, and wherein said piston forms a continuous fluid-tight seal with said wall of said chamber as said piston moves between said first and second positions;
   (e) means for biasing said piston towards said second position to thereby apply pressure to said liquid;
   (f) means for sterilizing said liquid within said chamber;
   (g) valve means for selectively opening and closing said fluid discharge port; and
   (h) fluid communication means communicating between said chamber and said fluid discharge port.

2. The device of claim 1 wherein said piston is hollow, having an open first end and a closed second end.

3. The device of claim 1, further comprising means for timing the sterilizing of said liquid.

4. The device of claim 1, wherein said means for sterilizing comprises electric heating means.

5. The device of claim 4, further comprising thermostat means for regulating the temperature of said liquid.

6. The device of claim 1, further comprising thermostat means for regulating said fluid discharge means.

7. The device of claim 1, further comprising pressure responsive closure means for locking said sealable opening, whereby pressure within said chamber prevents the removal of said closure means.

8. The device of claim 1, further comprising locking means for securing said piston in an extended position relative to said cylinder.

9. The device of claim 1, wherein said fluid discharge means further comprises a heated fluid delivery channel.

10. The device of claim 5, wherein said temperature regulating means comprises a housing, a pair of separated power supply electrodes in said housing, a rubber diaphragm mounted to contct said liquid, frame means mounted for movement in said housing and connected to said diaphragm, and electrodes mounted on said frame for intermittently forming and breaking a circuit with said power supply electrodes.

11. The device of claim 5, wherein said fluid discharge regulating means comprises a bi-metal strip immersed in said liquid and positioned to cause movement of a valve-locking element to prevent dispensing of said liquid when the temperature of said liquid exceeds a predetermined limit.

12. The device of claim 1 wherein said fluid communication means comprises a hollow tube aligned axially in said chamber and on which said piston is concentrically mounted for sliding movement.

13. The device of claim 1 further comprising means for timing the sterilizing of said liquid.

14. The device of claim 1 further comprising thermostat means for regualting the temperature of said liquid.

15. The device of claim 12 wherein said means for biasing comprises a coil spring mounted coaxially about said hollow tube.

16. The device of claim 1 further comprising a removable cap having said valve and one end of said hollow tube mounted therein.

17. The device of claim 16 wherein said valve comprises a body mounted for sealing, sliding movement within said one end of said hollow tube between a first closed position and a second open position, provided with a passageway therein for passage of said liquid to said discharge port when said body is in said open position, and further comprising means biasing said body to said closed position.

18. A device for sterilizing and storing liquids comprising:
   (a) a housing;
   (b) a collapsible closed chamber formed in said housing for receiving said liquid, said chamber provided with a sealable opening for introducing said liquid to said chamber and being collapsible between an expanded and a collapsed position;
   (c) means for biasing said chamber into said collapsed position thereby applying pressure to said liquid within said chamber;
   (d) means for sterilizing said liquid within said chamber; and
   (e) fluid discharge means for discharging said liquid when sterilized, further comprising a releasable valve.

* * * * *